US00PP21594P2

(12) United States Plant Patent
Wicki

(10) Patent No.: US PP21,594 P2
(45) Date of Patent: Dec. 28, 2010

(54) ***LOBULARIA* PLANT NAMED 'INLBUSNOPR'**

(50) Latin Name: ***Lobularia canariensis*×*Lobularia maritima***
Varietal Denomination: INLBUSNOPR

(75) Inventor: Peter Wicki, Canary Islands (ES)

(73) Assignee: Innova Plant GmbH & Co. KG, Gensingen (DE)

( * ) Notice: Subject to any disclaimer, the term of this patent is extended or adjusted under 35 U.S.C. 154(b) by 0 days.

(21) Appl. No.: 12/462,538

(22) Filed: Aug. 5, 2009

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—June Hwu
(74) *Attorney, Agent, or Firm*—C. A. Whealy

(57) ABSTRACT

A new and distinct cultivar of *Lobularia* plant named 'Inlbusnopr', characterized by its outwardly spreading, mounding and cascading plant habit; freely branching and vigorous growth habit; freely and continuous flowering habit; long flowering period; single flowers that are white in color; fragrant flowers; and good garden performance and tolerant to high temperatures.

1 Drawing Sheet

Botanical designation: *Lobularia canariensis*×*Lobularia maritima.*

Cultivar denomination: 'Inlbusnopr'.

BACKGROUND OF THE INVENTION

The present invention relates to a new and distinct cultivar of *Lobularia* plant, botanically known as *Lobularia canariensis*×*Lobularia maritima* and hereinafter referred to by the name 'Inlbusnopr'.

The new *Lobularia* plant is a product of a planned breeding program conducted by the Inventor in La Palma, Canary Islands, Spain. The objective of the breeding program was to develop new *Lobularia* plants with long-lasting fragrant flowers and high temperature tolerance.

The new *Lobularia* plant originated from a cross-pollination in March, 2005 in La Palma, Canary Islands, Spain of an unnamed selection of *Lobularia canariensis*, not patented, as the female, or seed, parent, with an unnamed selection of *Lobularia maritima*, not patented, as the male, or pollen, parent. The new *Lobularia* was discovered and selected by the Inventor as a single flowering plant within the progeny of the stated cross-pollination in a controlled greenhouse environment in La Palma, Canary Islands, Spain in April, 2006. Asexual reproduction of the new *Lobularia* plant by vegetative cuttings in a controlled greenhouse environment in La Palma, Canary Islands, Spain since April, 2007, has shown that the unique features of this new *Lobularia* plant are stable and reproduced true to type in successive generations.

SUMMARY OF THE INVENTION

Plants of the new *Lobularia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Inlbusnopr'.

These characteristics in combination distinguish 'Inlbusnopr' as a new and distinct cultivar of *Lobularia:*

1. Outwardly spreading, mounding and cascading plant habit.
2. Freely branching and vigorous growth habit.
3. Freely and continuous flowering habit.
4. Long flowering period.
5. Single flowers that are white in color.
6. Fragrant flowers.
7. Good garden performance and tolerant to high temperatures.

Plants of the new *Lobularia* differ from plants of the female parent selection in the following characteristics:

1. Plants of the new *Lobularia* are larger than plants of the female parent selection.
2. Plants of the new *Lobularia* have green-colored leaves whereas plants of the female parent selection have silvery grey-colored leaves.
3. Plants of the new *Lobularia* have larger flowers than plants of the female parent selection.
4. Plants of the new *Lobularia* flower for a longer period of time than plants of the female parent selection.

Plants of the new *Lobularia* differ from plants of the male parent selection in the following characteristics:

1. Plants of the new *Lobularia* are larger and bushier than plants of the male parent selection.
2. Plants of the new *Lobularia* have narrower leaves than plants of the male parent selection.

Plants of the new *Lobularia* can be compared to plants of *Lobularia maritima* 'Wonderland White', not patented. In side-by-side comparisons, plants of the new *Lobularia* differed from plants of 'Wonderland White' in the following characteristics:

1. Plants of the new *Lobularia* were more vigorous than plants of 'Wonderland White'.
2. Plants of the new *Lobularia* had larger flowers than plants of 'Wonderland White'.
3. Flowers of plants of the new *Lobularia* were more fragrant than flowers of plants of 'Wonderland White'.

4. Plants of the new *Lobularia* flowered for a longer period of time than plants of 'Wonderland White'.

Plants of the new *Lobularia* can also be compared to plants of *Lobularia maritima* 'Snow Crystals', not patented. In side-by-side comparisons, plants of the new *Lobularia* differed from plants of 'Snow Crystals' in the following characteristics:

1. Plants of the new *Lobularia* were more vigorous and more cascading than plants of 'Snow Crystals'.
2. Plants of the new *Lobularia* had larger flowers than plants of 'Snow Crystals'.
3. Flowers of plants of the new *Lobularia* were more fragrant than flowers of plants of 'Snow Crystals'.
4. Plants of the new *Lobularia* flowered for a longer period of time than plants of 'Snow Crystals'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Lobularia*.

The photograph at the bottom of the sheet comprises a side perspective view of a typical plant of 'Inlbusnopr' grown in a container.

The photograph at the top of the sheet is a close-up view of typical flowers of 'Inlbusnopr'.

DETAILED BOTANICAL DESCRIPTION

The aforementioned photographs and following observations, measurements and values describe plants grown in one-gallon containers in Bonsall, Calif., under commercial practice during the winter and spring in a polyethylene-covered greenhouse with day temperatures ranging from 20° C. to 27° C., night temperatures ranging from 9° C. to 13° C. and light levels ranging from 6,000 to 7,000 foot-candles. Plants were pinched two times and were four months old when the photographs and description were taken. In the following description, color references are made to The Royal Horticultural Society Colour Chart, 2007 Edition, except where general terms of ordinary dictionary significance are used.

Botanical classification: *Lobularia canariensis*×*Lobularia maritima* 'Inlbusnopr'.

Parentage:

*Female, or seed, parent.*—Unnamed selection of *Lobularia canariensis*, not patented.

*Male, or pollen, parent.*—Unnamed selection of *Lobularia maritima*, not patented.

Propagation:

*Type.*—Terminal vegetative cuttings.

*Time to initiate roots, summer.*—About 7 to 10 days at soil temperatures of about 16° C. to 18° C.

*Time to initiate roots, winter.*—About 7 to 10 days at soil temperatures of about 13° C. to 16° C.

*Time to develop roots, summer and winter.*—About two to three weeks at 13° C. to 18° C.

*Root description.*—Medium to thick in thickness, fibrous; white, close to 155D, in color.

*Rooting habit.*—Freely branching; dense.

Plant description:

*Form/habit.*—Annual flowering plant; indeterminate flowering habit; outwardly spreading, mounding and cascading plant habit; vigorous growth habit; freely branching habit with about eight to ten primary lateral branches and numerous secondary and tertiary lateral branches developing per plant; pinching enhances development of lateral branches.

*Plant height.*—About 15 cm.

*Plant diameter* (*area of spread*).—About 58 cm.

*Lateral branches.*—Length: About 40 cm. Diameter: About 4 mm. Internode length: About 1.2 cm to 3 cm. Texture: Sparsely pubescent. Color: Close to 146A.

Foliage description:

*Arrangement.*—Alternate; simple.

*Length.*—About 2.7 cm to 3.6 cm.

*Width.*—About 2.5 mm to 4 mm.

*Shape.*—Narrowly elliptical to lanceolate.

*Apex.*—Acute.

*Base.*—Attenuate.

*Margin.*—Entire.

*Texture, upper and lower surfaces.*—Pubescent.

*Color.*—Developing leaves, upper surface: Close to 137B. Developing leaves, lower surface: Close to 137C. Fully expanded leaves, upper surface: Close to 137A; venation, close to 137B. Fully expanded leaves, lower surface: Close to 137B; venation, close to 137C.

*Petioles.*—Length: About 4 mm. Diameter: About 1 mm. Texture, upper and lower surfaces: Pubescent. Color, upper surface: Close to 138A. Color, lower surface: Close to 138B.

Flower description:

*Flower type and habit.*—Small single rounded flowers arranged in indeterminate racemes; flowers face upward or outward; very freely flowering habit, about 24 open flowers per inflorescence.

*Natural flowering season.*—Long flowering period; in Southern California plants flower from March through October; flowering continuous during this period.

*Flower longevity on the plant.*—About three to four days; flowers not persistent.

*Fragrance.*—Fragrant; sweet, vanilla-like.

*Inflorescence height.*—About 10 cm to 16 cm.

*Inflorescence diameter.*—About 2.6 cm.

*Flower diameter.*—About 7 mm.

*Flower depth* (*height*).—About 3 mm.

*Flower buds.*—Length: About 2.5 mm. Diameter: About 2 mm. Shape: Roughly spherical. Color: Close to 137C.

*Petals.*—Quantity/arrangement: Four petals fused in a single whorl. Length: About 4 mm. Width: About 4 mm. Shape: Oval to roughly reniform. Apex: Rounded. Base: Attenuate to truncate. Margin: Entire. Texture, upper and lower surfaces: Smooth, glabrous. Color: When opening, upper and lower surfaces: Close to NN155A. Fully opened, upper and lower surfaces: Close NN155A.

*Sepals.*—Arrangement/appearance: Single whorl of four sepals. Length: About 2 mm. Width: About 1 mm. Shape: Elliptical. Apex: Acute. Base: Truncate. Margin: Entire. Texture, upper surface: Smooth, glabrous. Texture, lower surface: Sparsely pubescent. Color, upper surface: Close to 144A. Color, lower surface: Close to 144B.

*Peduncles.*—Length: About 3 cm. Width: About 2 mm. Strength: Strong. Texture: Sparsely pubescent. Color: Close to 146B.

*Pedicels.*—Length: About 6 mm. Width: About 1 mm. Strength: Moderately strong. Texture: Smooth, glabrous. Color: Close to 146C.

*Reproductive organs.*—Stamens: Quantity per flower: Five. Filament length: About 2 mm. Filament color: Close to 145B. Anther shape: Oval to almost lanceolate. Anther length: Less than 1 mm. Anther color: Close to 13C. Pollen amount: None observed. Pistils: Quantity per flower: One. Pistil length: About 2 mm. Style length: Less than 1 mm. Style color: Close to 138B. Stigma shape: Globular. Stigma color: Close to N144A. Ovary color: Close to 144A.

*Seed/fruit.*—Seed and fruit production have not been observed.

Pathogen/pest resistance: Plants of the new *Lobularia* have not been noted to be resistant to pathogens or pests common to *Lobularia*.

Garden performance: Plants of the new *Lobularia* have been observed to have good garden performance and have been noted to tolerate temperatures from about 1° C. to about 32° C. and have excellent tolerance to rain and wind.

It is claimed:

1. A new and distinct *Lobularia* plant named 'Inlbusnopr' as illustrated and described.

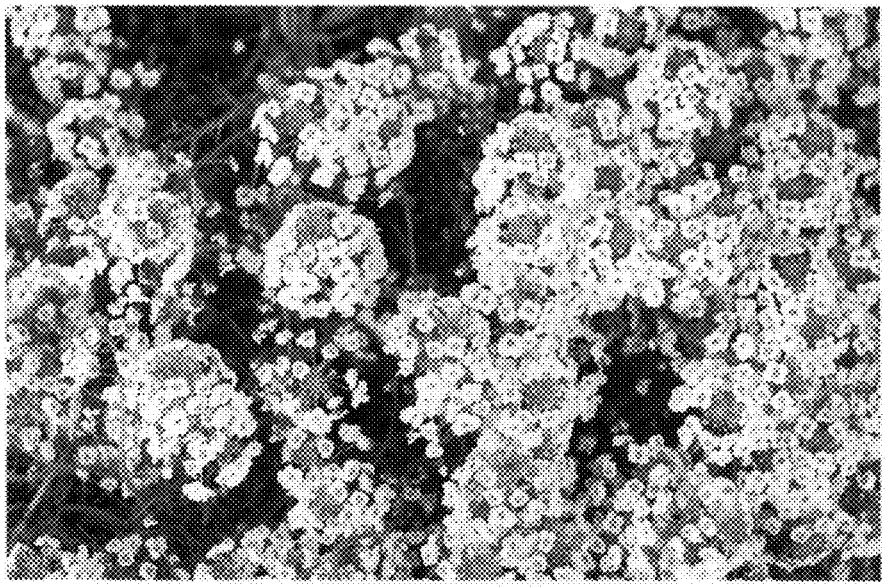
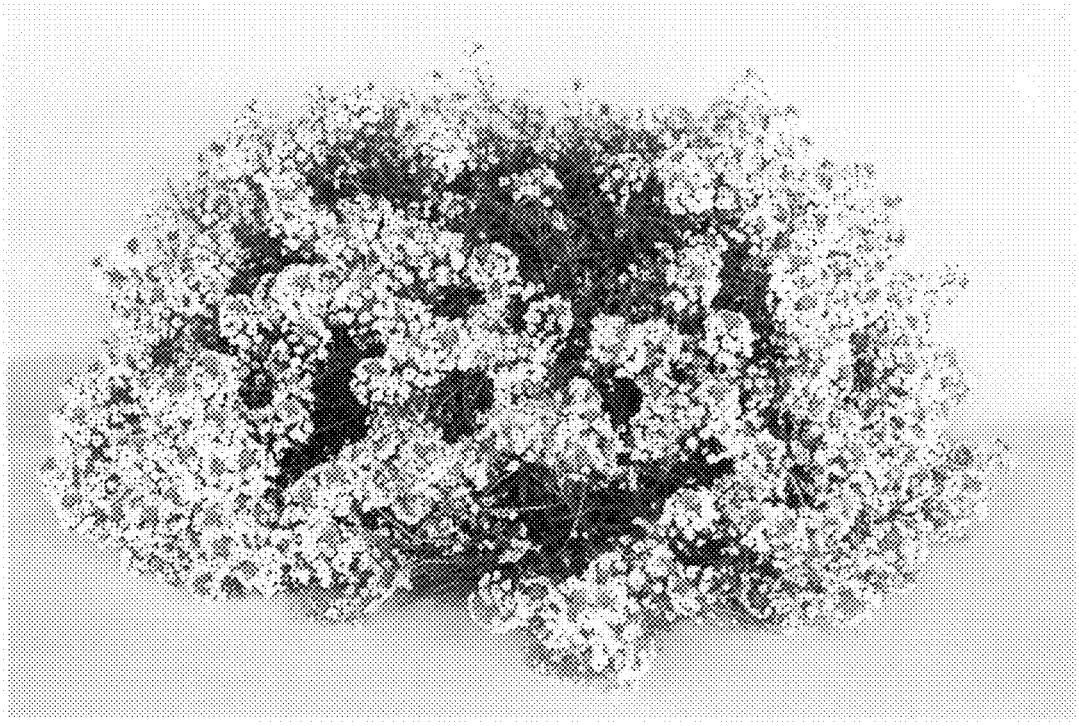

* * * * *